US00PP13445P2

(12) United States Plant Patent
Oliver

(10) Patent No.: US PP13,445 P2
(45) Date of Patent: Dec. 31, 2002

(54) TIARELLA PLANT NAMED 'PINK PEARLS'

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 09/968,318

(22) Filed: Sep. 30, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Annette Para
(74) *Attorney, Agent, or Firm*—C. A. Whealy

(57) ABSTRACT

A distinct cultivar of Tiarella plant named 'Pink Pearls', characterized by its mounded plant habit; vigorous and robust growth habit; numerous white showy flowers arranged on dense racemes; long flowering period; and excellent garden performance.

1 Drawing Sheet

BOTANICAL CLASSIFICATION

*Tiarella unifoliata*×*Tiarella cordifolia.*

VARIETY DENOMINATION

'Pink Pearls'.

BACKGROUND OF THE INVENTION

The present invention relates to a new and distinct cultivar of Tiarella plant, botanically known as *Tiarella unifoliata*× *Tiarella cordifolia* and hereinafter referred to by the name 'Pink Pearls'.

The new Tiarella is a product of a planned breed program conducted by the Inventor in Scottdale, Pa. The objective of the breeding program is to create new vigorous Tiarella cultivars that have a long flowering period and showy and attractive flower and leaf coloration.

The new Tiarella was discovered by the Inventor in a controlled environment in Scottdale, Pa., from seedling progeny from a cross-pollination made by the Inventor in May, 1994, of an unnamed selection of *Tiarella unifoliata*, not patented, as the female, or seed, parent with the *Tiarella cordifolia* cultivar George Schenk, not patented, as the male, or pollen, parent. The new Tiarella was selected by the Inventor in May, 1995. The selection of this plant was based on its plant size and desirable leaf and flower coloration.

Asexual reproduction of the new Tiarella by cuttings taken in a controlled environment in Scottdale, Pa., since August, 1995, has shown that the unique features of this new Tiarella are stable and reproduced true to type in successive generations.

SUMMARY OF THE INVENTION

The cultivar Pink Pearls has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Pink Pearls'. These characteristics in combination distinguish 'Pink Pearls' as a new and distinct cultivar:

1. Full and densely foliated; mounded plant habit.
2. Vigorous and robust growth habit.

3. Numerous white showy flowers arranged on dense racemes.
4. Long flowering period.
5. Excellent garden performance.

Plants of the new Tiarella differ from plants of the female parent, the unnamed selection of *Tiarella unifoliata*, in side-by-side comparisons conducted by the Inventor in Scottdale, Pa. in the following characteristics:

1. Plant habit of plants of the new Tiarella is compact and mounded whereas plant habit of plants of the unnamed selection of *Tiarella unifoliata* is open and spreading.
2. Leaves of plants of the new Tiarella are glossier and not as pubescent as leaves of plants of the unnamed selection of *Tiarella unifoliata.*
3. Plants of the new Tiarella have dense racemes whereas plants of the unnamed selection of *Tiarella unifoliata* have sparse racemes.
4. Plants of the new Tiarella flower for a longer period of time than plants of the unnamed selection of *Tiarella unifoliata.*
5. Plants of the new Tiarella are more hardy than plants of the unnamed selection of *Tiarella unifoliata.*

Plants of the new Tiarella differ from plants of the male parent, the cultivar George Schenk, in side-by-side comparisons conducted by the Inventor in Scottdale, Pa in the following characteristics:

1. Plant habit of plants of the new Tiarella is more outwardly spreading than plant habit of plants of the cultivar George Schenk.
2. Plants of the new Tiarella are larger, more vigorous and more robust than plants of the cultivar George Schenk.
3. Racemes of plants of the new Tiarella are more outwardly spreading and not as erect as racemes of plants of the cultivar George Schenk.
4. Plants of the new Tiarella have white-colored flowers whereas plants of the cultivar George Schenk have pink-colored flowers.
5. Plants of the new Tiarella flower for a longer period of time than plants of the cultivar George Schenk.

Plants of the new Tiarella can be compared to plants of the cultivar Tiger Stripe, not patented. In side-by-side comparisons conducted by the Inventor in Scottdale, Pa., plants of the new Tiarella differed from plants of the cultivar Tiger Stripe in the following characteristics:

1. Plant habit of plants of the new Tiarella is more outwardly speading than plant habit of plants of the cultivar Tiger Stripe.

2. Leaves of plants of the new Tiarella are solid green in color whereas leaves of plants of the cultivar Tiger Stripe are green with extensive and variable dark purple markings.

3. Racemes of plants of the new Tiarella are more outwardly spreading than racemes of plants of the cultivar Tiger Stripe.

4. Plants of the new Tiarella have white-colored flowers whereas plants of the cultivar Tiger Stripe have pink-colored flowers.

5. Plants of the new Tiarella flower for a longer period of time than plants of the cultivar Tiger Stripe.

Plants of the new Tiarella can also be compared to plants of the cultivar Elizabeth Oliver, not patented. In side-by-side comparisons conducted by the Inventor in Scottdale, Pa., plants of the new Tiarella differed from plants of the cultivar Elizabeth Oliver in the following characteristics:

1. Plants of the new Tiarella are larger than plants of the cultivar Elizabeth Olive.

2. Leaves of plants of the new Tiarella are green in color whereas leaves of plants of the cultivar Tiger Stripe are green with dark purple coloration towards the leaf base.

3. Racemes of plants of the new Tiarella are taller than racemes of plants of the cultivar Elizabeth Oliver.

4. Plants of the new Tiarella have white-colored flowers whereas plants of the cultivar Elizabeth Oliver have pink-colored flowers.

5. Plants of the new Tiarella flower for a longer period of time than plants of the cultivar Elizabeth Oliver.

BRIEF DESCRIPTION OF THE PHOTOGRAPHS

The accompanying colored photographs illustrate the overall appearance of the new Tiarella, showing the colors as true as it is reasonably possible to obtain in colored reproductions of this type. Colors in the photographs may differ slightly from the color values cited in the detailed botanical description which accurately describe the colors of the new Tiarella. The photograph comprises a side perspective view of a typical flowering plant of 'Pink Pearls'.

DETAILED BOTANICAL DESCRIPTION

In the following description, color references are made to The Royal Horticultural Society Colour Chart except where general terms of ordinary dictionary significance are used. The following observations and measurements describe pinched plants grown in Keller, Tex. during the summer and fall outdoors under full sun and cultural conditions which approximate commercial practice. Plants used for the photographs and descriptions were grown as single plants in one-gallon containers and were about one year old. Measurements and numerical values represent averages taken from a group of flowering plants.

Botanical classification: *Tiarella unifoliata*×*Tiarella cordifolia* cultivar Pink Pearls.

Parentage:

*Female, or seed, parent.*—Unnamed selection of *Tiarella unifoliata*, not patented.

*Male, or pollen, parent.*—*Tiarella cordifolia* cultivar George Schenk, not patented.

Propagation:

*Type.*—By cuttings.

*Time to initiate roots.*—About 14 days at 23° C.

*Time to produce a rooted cutting.*—About 30 days at 23° C.

*Root description.*—Fine, fibrous and well-branched.

Plant description:

*Appearance.*—Perennial; basal rosette plant habit with leaves developing from the base; densely foliated; full, mounded plant habit with upright to outwardly spreading racemes with showy white-colored flowers. Vigorous and robust growth habit.

*Plant size.*—Height: Soil level to top of foliar plane: About 15 cm. Soil level to top of racemes: About 32 cm. Diameter or spread: About 31 cm.

*Foliage description.*—Arrangement: Basal rosette, single. Length: About 7.5 cm. Width: About 7.1 cm. Shape: Roughly cordate. Apex: Acute. Base: Cordate. Margin: Crenate and serrulate with ciliation. Texture: Upper surface, uniformly distributed pubescence; lower surface pubescence mostly along the main veins. Venation pattern: Palmate. Color: Young foliage, upper surface: Close to between 146A and 146B. Young foliage, lower surface: Close to 147C. Mature foliage, upper surface: Darker and more green than 146A. Mature foliage, lower surface: Close to 147B to 147C. Venation, upper surface: Similar to ground color. Venation, lower surface: Similar to ground color. Petiole: Length: About 9.3 cm. Diameter: About 2 mm. Strength: Moderately strong; flexible and wiry. Texture, upper and lower surfaces: Densely pubescent. Color, upper and lower surfaces: 146B to 146C.

Flower description:

*Appearance/arrangement.*—Single campanulate flowers arranged on numerous erect to outwardly spreading and dense racemes; racemes, cylindrical arrangement with at least 70 flowers and flower buds per flowering stem and about three flowers per lateral pedicel. Flowers face mostly outward. Flowering continuous with at least 12 flowering stems per plant developing throughout the flowering period. Flowers not persistent. Flowers not fragrant.

*Time of flowering.*—Long flowering period; under natural conditions, plant flower from the late spring through mid-summer.

*Inflorescence longevity.*—Individual inflorescences about one week on the plant.

*Inflorescence size.*—Length: About 16.1 cm. Diameter: About 2.1 cm.

*Flower size.*—Diameter: About 4.5 mm. Depth (height): About 3.5 mm.

*Flower buds.*—Height: About 1.25 mm. Diameter: About 2 mm. Shape: Ovoid to spherical. Color, at stage of showing color: Pink; white, 155D, ground color overlain with red purple, close to 59A.

*Petals.*—Quantity/arrangement: Five petals; radially symmetrical and fused at base. Length: About 3 mm. Width: Less than 1 mm. Shape: Narrowly elongate. Apex: Acute. Margin: Entire. Texture: Pubescent. Color: When opening, upper and lower surfaces: White, close to 155D with occasional red purple, close to 59A, spots. Fully opened, upper and lower surfaces: White, close to 155D.

*Sepals.*—Quantity/arrangement: Five sepals; radially symmetrical and fused at base. Length: About 3.5 mm. Width: About 1.8 mm. Shape: Elongated oblong. Apex: Acute. Margin: Entire. Texture: Pubescent. Color: When opening, upper and lower surfaces: White, close to 155D, with small red purple, close to 59A, spots. Fully opened, upper and lower surfaces: White, close to 155D, with few small red purple, close to 59A, spots.

*Bracts.*—Quantity/arrangement: One at base of flower. Length: About 2 mm. Width: Less than 1 mm. Shape: Roughly ovate. Apex: Sharply acute. Base: Attenuate, sessile. Margin: Serrate with ciliation. Texture: Pubescent. Color, upper and lower surfaces: Close to 146B.

*Peduncle.*—Strength: Moderately strong; flexible. Aspect: Erect to about 45° from vertical. Length: About 31.5 cm. Diameter: About 2 mm. Texture: Pubescent. Color: Immature: Between 146A and 146B; towards apex, overlain with anthocyanin, close to 187A. Mature: Between 146A and 146B.

*Pedicels.*—Strength: Moderately strong; flexible and wiry. Aspect: About 45° from vertical. Length: About 2.1 mm. Diameter: Less than 1 mm. Texture: Pubescent. Color: 146A to 146B; towards the apex occasionally overlain with anthocyanin, close to 187A.

*Reproductive organs.*—Androecium: Stamen number: Ten per flower. Anther shape: Bi-lobed. Anther length: Less than 1 mm. Anther color: Close to 7A. Amount of pollen: None observed. Gynoecium: Pistil number: One per flower. Pistil length: About 3 mm. Stigma shape: Rounded. Stigma color: Close to 155D. Style color: Close to 155D. Ovary color: Close to 155D.

*Seed/fruit.*—Seed/fruit production has not been observed.

Disease pest resistance: Resistance to pathogens and pests common to Tiarella has not been observed on plants grown under commercial conditions.

Temperature tolerance: Plants of the new Tiarella have demonstrated good tolerance to night temperatures as low as −30° C and day temperatures as high as 45° C.

It is claimed:

1. A new and distinct cultivar of Tiarella plant named 'Pink Pearls', as illustrated and described.

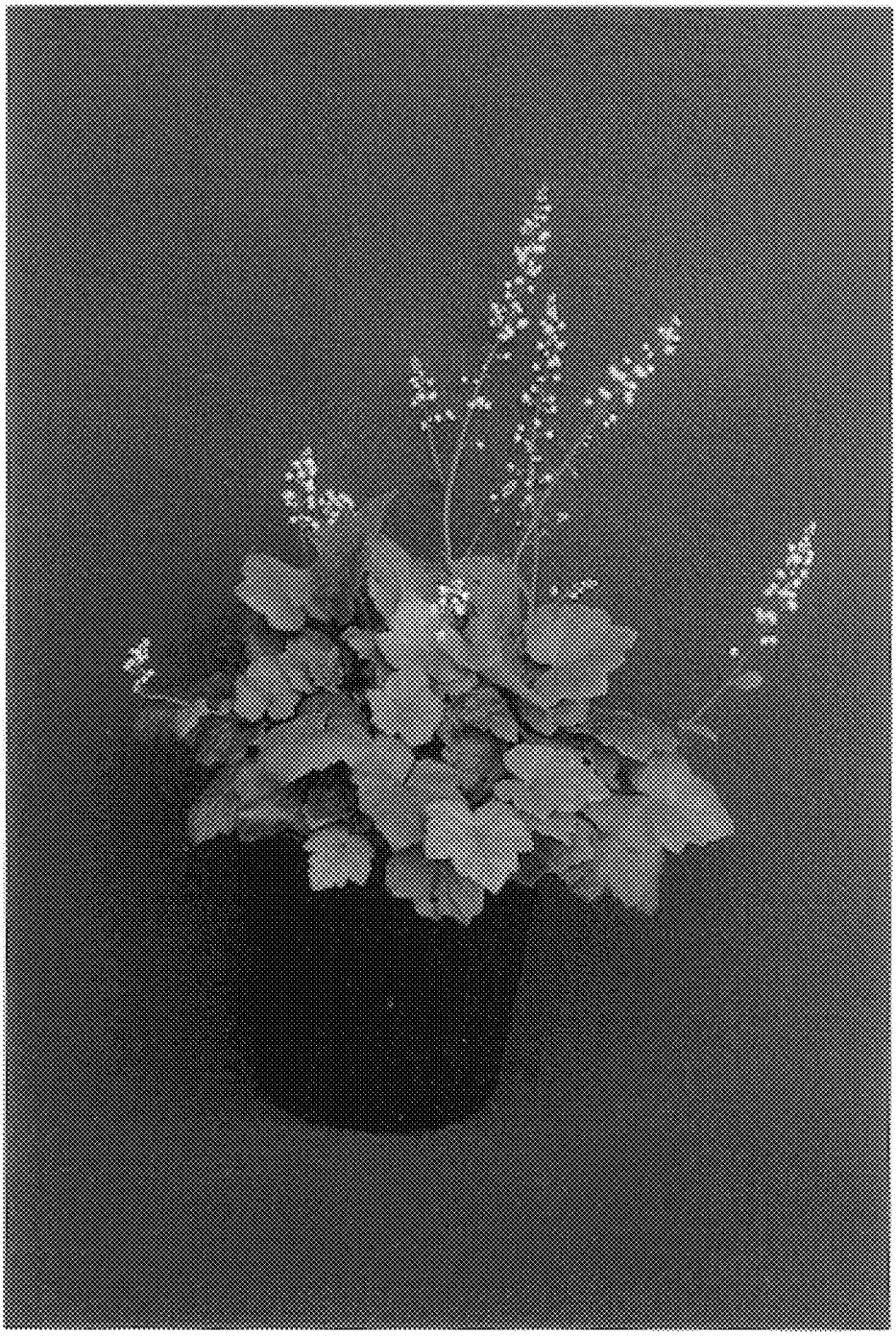

* * * * *